US012390651B2

(12) United States Patent
Taff et al.

(10) Patent No.: US 12,390,651 B2
(45) Date of Patent: Aug. 19, 2025

(54) COMMUNICATION SYSTEM AND METHOD FOR AN IMPLANTABLE MEDICAL DEVICE

(71) Applicant: BIOTRONIK SE & Co. KG, Berlin (DE)

(72) Inventors: Brian M. Taff, Portland, OR (US); Kurt Swenson, Dayton, OR (US); Dean Bergstrom, West Linn, OR (US); Julian Merlin, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 18/558,555

(22) PCT Filed: May 18, 2022

(86) PCT No.: PCT/EP2022/063418
§ 371 (c)(1),
(2) Date: Nov. 2, 2023

(87) PCT Pub. No.: WO2022/248303
PCT Pub. Date: Dec. 1, 2022

(65) Prior Publication Data
US 2024/0139527 A1    May 2, 2024

Related U.S. Application Data

(60) Provisional application No. 63/193,303, filed on May 26, 2021.

(30) Foreign Application Priority Data

Jul. 2, 2021   (EP) .................................. 21183353

(51) Int. Cl.
*A61N 1/372*    (2006.01)
*A61N 1/365*    (2006.01)

(52) U.S. Cl.
CPC ...... *A61N 1/37252* (2013.01); *A61N 1/37235* (2013.01); *A61N 1/365* (2013.01)

(58) Field of Classification Search
CPC ...................... A61N 1/37252; A61N 1/37235
See application file for complete search history.

(56) References Cited

U.S. PATENT DOCUMENTS 10,182,336 B1    1/2019  Stockton et al.
2005/0033982 A1*  2/2005  Paaske .................. G06F 21/552
                                                             726/27

(Continued)

FOREIGN PATENT DOCUMENTS

WO    2019126101 A1    6/2019

OTHER PUBLICATIONS

International Search Report (PCT/ISA/210) and Written Opinion (PCT/ISA/237) mailed on Jul. 8, 2022, by the European Patent Office as the International Searching Authority for International Application No. PCT/EP2022/063418. (9 pages).

*Primary Examiner* — Brian T Gedeon
(74) *Attorney, Agent, or Firm* — Buchanan Ingersoll & Rooney PC (57) ABSTRACT

The invention is directed to a communication system for a wireless message transfer between an implantable medical device (IMD) and an external device. A communication system is disclosed that effectively throttles/manages messages in a limited resource communication scheme, wherein the IMD is configured to monitor the health status of a patient and/or configured to deliver a therapy signal to the patient, wherein the IMD comprises a processor and a transceiver module configured to bi-directionally exchange the messages with the external device, wherein the processor adopts at least a predefined active state and a predefined processing state, wherein the processor of the IMD is configured to produce response messages in order to send (Continued)

these response messages from the transceiver module to the external device. The invention is further directed to a respective communication method, computer program product and computer readable data carrier.

8 Claims, 2 Drawing Sheets

(56) References Cited

U.S. PATENT DOCUMENTS

| | | |
|---|---|---|
| 2017/0056677 A1 | 3/2017 | Zhang et al. |
| 2017/0312530 A1 | 11/2017 | Schilling et al. |
| 2020/0221263 A1 | 7/2020 | Sturman et al. |
| 2021/0315031 A1* | 10/2021 | Wu .................. H04W 84/18 |

* cited by examiner

COMMUNICATION SYSTEM AND METHOD FOR AN IMPLANTABLE MEDICAL DEVICE

CROSS-REFERENCE TO RELATED APPLICATIONS

This application is the United States National Phase under 35 U.S.C. § 371 of PCT International Patent Application No. PCT/EP2022/063418, filed on May 18, 2022, which claims the benefit of European Patent Application No. 21183353.8, filed on Jul. 2, 2021, and U.S. Provisional Patent Application No. 63/193,303, filed on May 26, 2021, the disclosures of which are hereby incorporated by reference herein in their entireties.

TECHNICAL FIELD

The present invention is directed to a communication system for data transfer between an implantable medical device (IMD) and an external device, wherein the IMD is configured to monitor the health status of a patient and/or configured to deliver a therapy signal to the patient. The external device is located at least partially extracorporeally. The present invention is further directed to a respective method for data transfer, a respective computer program and a respective computer readable data carrier. The computer program product may be a software routine, e.g., related to hardware support means within the IMD and/or the external device.

BACKGROUND

Active and passive implantable medical devices (IMDs), for example, a pacemaker (with leads), an Implantable Cardiac Monitor (ICM), an Implantable Leadless Pacer (ILP), an Implantable Leadless Pressure Sensor (ILPS), an Implantable Cardiac Defibrillator (ICD) or a Subcutaneous Implantable Cardiac Defibrillator (i.e., S-ICD), contain sensors that collect physiological signals in order to monitor the health status of the patient and transmit them as data to an physician device or to a remote server using the external device. The data collected from these various or any such sensors can include, but are not limited to, ECG, impedance, activity, posture, heart sounds, pressure, respiration, and other data. Active IMDs, (e.g., pacemaker, ILP, ICD, or S-ICD) may provide therapy output to the patient, for example electrical stimulation within a heart chamber (e.g., atrium or ventricle).

Usually, such IMDs comprised of a processor for data processing and a transceiver module configured to bi-directionally exchange messages with the external device if, for example, implanted within the body of the patient. The external device, possibly using its own transceiver, is also configured for bi-directionally exchange messages with the transceiver module of the IMD. The external device may be a separate device connected to a computer (in some cases called programmer) or may be a module integrated within a remote device such as a computer. The external device produces and sends messages to the transceiver of the IMD in form of requests, for example for receiving data concerning the health status of the patient or IMD status from the IMD or for programming (in order to configure the IMD to apply appropriate therapies to the patient).

Processing data, applying algorithms to the data or having the IMD drive the management of communication with the external device presents challenges and drawbacks due to the low-power requirements and limited computational resources within the IMD. The bulk of the management of such routines cannot be performed within the IMD without risking problematic impacts on device longevity. To extend IMD longevity (providing a best access to meaningful clinical benefit), there is a demand to house more power/energy within the IMD. Unfortunately, if such power/energy cannot be incorporated within the IMD through high power/energy dense battery chemistries, access to these increased longevities can demand that larger batteries be used. Given the small size of state-of-the-art IMDs, if built with larger batteries there is a risk for increasing the physical size of the IMD, which akin to compromised longevity is also clinically undesirable (especially for leadless pacemaker IMD—a device type stationed within the heart volume). Accordingly, the communication infrastructure and message processing need in an IMD system must be optimized for low energy operation.

Such optimized communication and messaging should furthermore avoid overloading communication infrastructures (e.g., information routing on a bus or otherwise) and appropriately structure the command/response dynamic 1.) in ways that an in-system command initiation source, such as the external device, is informed of the processing of its instated requests by downstream handlers such as the IMD,
2.) in ways where the IMD can avoid any sort of problematic processing that might occur subject to repeated requests from the external device (i.e., in cases where the external device was unaware that the IMD had the request and therefore "retried"), and
3.) in ways that offer means for managing the navigation through in-IMD data memory without introducing unwanted overhead.

It is known for communication protocols/architectures to include a capacity of some sort to poll the status of in-system data processing units. Such support often embodies a "ping" request from one or more in-system command initiation sources to which downstream handlers can report on progress in servicing previously issued requests (e.g., the task completion bars often seen in Windows Application installation processes). Such conditions can take a multitude of forms with varying degrees of complexity, but often amount to a specific command or series of commands that ask the downstream handlers "Are you finished?". However, such communication procedures can impose excessive crowding of the data message link between an IMD and an external device, challenging the system's ability to efficiently handle requests and data transfer in ways that are not protracted in duration.

In communication systems it is furthermore common for systems to include architectural features in downstream handlers that prevent complications/challenges subject to repeated bombardment by upstream command initiation sources that instate calls to action. Such mechanisms often embody a buffers or stacks within the downstream handlers that can retain such requests. In best embodiments such systems might pile up a list of commands that have been requested in a specific order and then, as the data handlers complete earlier requests, the local buffer can be "popped" to proceed with further action. Additionally, with appropriate smarts, the features that load the buffer can filter for command repeats and only load the buffer/stack with new items. This approach can add interpretation, handling, and management complexity to in-system units (i.e., the downstream handlers) which are misaligned with the computational and storage resources available within.

Accordingly, it is desirable to provide a communication system and method that effectively throttles/manages messages in a limited resource communication scheme.

The present disclosure is directed toward overcoming one or more of the above-mentioned problems, though not necessarily limited to embodiments that do.

SUMMARY

At least the above problem is solved by a communication system for data transfer between an IMD and an external device, by a respective communication method, by a computer program product, and by a computer readable data carrier.

In particular, at least the above problem is solved by a communication system for, in particular, wireless data transfer between an implantable medical device (IMD) and an external device, wherein the IMD is configured to monitor the health status of a patient and/or configured to deliver a therapy signal to the patient, wherein the IMD comprises a processor and a transceiver module configured to bi-directionally exchange messages with the external device (if the IMD is, for example, implanted within the body of the patient), wherein the processor adopts at least a predefined active state and a predefined processing state, wherein processor of the IMD is configured to produce response messages in order to send these response messages from the IMD's transceiver module to the external device, wherein each response message comprises a processor state field or section at a predefined location within the response message wherein
  a predefined first value is assigned to the processor state section as long as the processor is currently (i.e., at the moment) in a predefined processing state and
  a predefined second value different from the first value is assigned to the processor state section if the processor is currently (i.e., at the moment) not in the processing state.

The IMD is an implantable medical device as defined above configured to monitor the health status of a patient and/or configured to deliver a therapy signal to the patient.

Since the processor state field might be longer than 1 bit, the values can also be defined as follows:
  a predefined first set of values is assigned to the processor state field as long as the processor is currently in a predefined processing state and
  a predefined second value different from the first values is assigned to the processor state field if the processor is currently not in the processing state.

Alternatively or additionally, different states could be defined which reflect different levels of susceptibility for certain types or sets of request messages, i.e., like exposing a current processor/task priority to the external device telling what type of request is accepted by the IMD to interrupt the current ongoing processor activity.

The IMD comprises a processor for data processing and a transceiver module (e.g., a coil connected to an appropriate communication management capability or an antenna) for sending messages (i.e., communication signals) from and transmitting messages to the external device. The messages sent by the transceiver module of IMD are called "response messages" in the following. Messages are strings of bits embedded in a syntax and semantics system defined as part of a communication protocol expressed in and interpreted by well-defined algorithms and data structures. The messages received by the IMDs transceiver module, also called request messages, are relayed to the processor for data processing. Analogously, the processor produces the content of the signals/messages which are subsequently relayed to the transceiver module for sending to the external device as response messages.

The IMD may comprise further modules such as a memory for storing data, a power supply inclusive of battery support or otherwise, at least one sensor for retrieving physiological signals from the patient and/or a signal generator for generating and administering, for example, electrical or electromagnetic therapy signals. The transceiver module, the memory, the power supply, the at least one sensor and/or the signal generator may be electrically connected to the processor.

The memory of the IMD may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device.

The external device is located at least partially extracorporeally and may be a separate module wirelessly or by-wire connected to a computer (e.g., physician device, remote server, programmer) having a processor. Alternatively, the external device may be an integrated unit of such computer, for example, may form an integrated unit of the programmer. For bi-directional communication the external device may comprise a transceiver for messages (signals), for example, a coil connected to a communication module or an antenna. The communication module may comprise or interface with a processor, in particular, if it is a module separate from a computer.

Wireless communication of the external device and the IMD comprises communication over the air (without wire). The communication may use inductive magnetic means, acoustic methods (e.g., ultrasound), and/or acoustic, optical and/or electromagnetic waves, for example Bluetooth, WLAN, ZigBee, NFC, Wibree or WiMAX in the radio frequency region, or IrDA or free-space optical communication (FSO) in the infrared or optical frequency region.

With regard to the present invention each processor is regarded as a functional unit of the IMD, the external device and/or the computer, respectively, that interprets and executes instructions comprising an instruction control unit and an arithmetic and logic unit. The (remote) computer or external device, i.e., a functional unit that can perform substantial computations, including numerous arithmetic operations and logic operations without human intervention, such as, for example, a personal mobile device (PMD), a desktop computer, a server computer, clusters/warehouse scale computer or embedded system.

According to the present invention, the processor of the IMD adopts at least an active state and/or a processing state. In the processing state the processor must either collect, gather, or ship internally-stored data outbound (in one or more responses) or control or take actions to collect measurements or run routines, (e.g., for therapy application), for periods of time that delay the IMD's capacity to immediately respond. Accordingly, in the processing state, the processor operates to respond to an external request and/or to process data according to an internal routine/algorithm. In the following, the processing state is also called the 'busy state'. When the IMD's communication support is not in the 'busy state' but engaged in a communication link with the external device it simply resides in an 'active state' (where the transceiver is ON and the IMD is ready for further interaction with the external device). In the active state, the processor is not 'busy' and is capable of receiving requests from an external device that may be subsequently handled. Conditions where the processor may change from the 'active state' (i.e., an initial standby state) to the 'processing state' may be predefined and, for example, stored in a data memory of the IMD or the handling of any specific request from the external device and the emergent, resulting durations needed for such handling may simply instate such transitions. After finishing the respective task that has held the IMD in a 'busy state" the processor switches back to the 'active state'.

To inform the external device about the state of the processor, according to the present invention, each response message sent by the IMD (i.e., by its transceiver module) comprises a processor state field at a predefined location within the response message wherein
- a predefined first value is assigned to the processor state field as long as the processor is currently in a predefined processing state and
- a predefined second value different from the first value is assigned to the processor state field if the processor is currently not in the processing state.

The location (information) may be a single bit within a wrapper (i.e., non-payload portion). This bit is at a location understood by both the sender and the receiver in the communication system. It literally does not matter where this bit resides within the message as long as it is a location known/understood by both the sender and the receiver. It could be the first bit or some other bit. It's likely not the last bit because a signature check often resides at the end of the message, but there is no rule that would force such a design.

All messages transmitted by the IMD involve the processor of the IMD assigning at least the first value or the second value, respectively, as defined above, to the processor state field within the transmitted message. Transmission of additional values within this field is thereby not excluded but depends on the length of the field. In one embodiment the length of the processor state field is 1 bit to 4 bits. In case, the processor state field is 1 bit ('busy bit'), the first value may be the value 1 and the second value may be the value 0, for example. This most simplified approach would mean that the IMD reports (through the processor state field) whether or not the processor has completed processing tasks from the last received request message using a lone YES/NO-, BUSY/NOT BUSY-, 1/0-style toggle.

Above the means for the command source (external device) to determine the readiness of the command handler (IMD) are described. This is also used by the command source (external device) to restrict sending of additional commands until the command handler (IMD) is ready to receive a command. Furthermore, the command source (external device) may send additional non-commands that poll for updates to this status.

In one embodiment, the external device receiving a response message from the IMD containing the first value assigned to the processor state field is configured to pause in sending any new request messages to the transceiver module of the IMD until the external device receives a message containing the second value assigned to the processor state field. Such request messages which require waiting may be predefined and, for example, stored in a data memory of the external device, or as noted earlier busy status may simply emerge from prevailing conditions within the IMD that lengthen processing durations when handling any received requests/instructions.

The above defined leadless communication scheme is based on the notion of single-treaded command processing. Within this context, new commands cannot be processed until the current command's processing and handling has been completed by the IMD. Cases where such support proves especially relevant are seen in device follow-up interrogation, programming, and testing routines. According to the present invention, the IMD offers a means to report its predefined processing state (i.e., the 'in progress' or 'busy' status) to the user-side infrastructure (i.e., the external device) as a means to avoid facing a congestion of requests that would break the single-threaded architecture. According to the present invention, a processor state section is incorporated in messages relayed from the IMD and used of as part of leadless system packet design to enable IMD status communication that supports the throttling of new requests from external device side resources prior to the completion of any handling affiliated with prior received requests.

The communication system according to the present invention provides active feedback within a leadless communication infrastructure regarding the processing state of the processor of the IMD to avoid overwhelming the limited resource system with a flood of request messages that might challenge efforts to optimize higher-level feature support. The communication system offers a bandwidth saving handshake mechanism for data relay between the sender (i.e., the external device) and the receiver (i.e., the IMD) as command data can be managed without unnecessarily hampering support for passing real-time streaming data from the IMD to the external device.

In one embodiment, the request message (message sent by the external device to the IMD) is a proximity request message (i.e., a regular request from the external device, sent at specified time intervals) nominally intended to maintain the data link between the IMD and the external device (also called proximity command relay); a monitoring request message (i.e., a request for determining a certain actual physiological signal stored within or collectable by the IMD); a data request message (i.e., a request for delivery of certain data stored or parameter states within the IMD); a program write message (i.e., an instruction for setting a certain therapy parameter or otherwise); a status request message (i.e., a request for providing conditions of a status parameter such as the battery's state of charge); or an execution request message (i.e., a request for execution of a specified routine or program sequence).

In one embodiment, the external device is receiving a response message from the IMD containing the first value assigned to the processor state field is configured to wait with sending certain types of new request messages to the transceiver module of the IMD until the most recent response message contains the second value assigned to the processor state field.

In one embodiment, the response message (message sent by the IMD to the external device) is a proximity response message (i.e., a response to a proximity request message) or a reporting response message (i.e., a response to a monitoring, data request, program, or execution request message), the latter transmitted after the IMD's completion of any necessary handling. A nominally instantaneous response in cases where the IMD's resultant duty centers on simply only informing the external device that the IMD received the respective request (i.e., an acknowledge response).

In one embodiment, the response message is a proximity response message, a status reporting response message, a data payload/relay response message, a response message carrying measurement data acquired through triggered routines instated by the external device, or an acknowledgement response message.

Additionally or alternatively, the external device may be configured to produce transmit request messages in order to send these messages to the transceiver module of the IMD, wherein each request message comprises a sequence field at a predefined location within the request message which is toggled between at least a first value and a second value associated to the sequence section, wherein a second request message contains the toggled second value if the external device received a valid response from the IMD to the immediately previously sent first request message containing the first value or vice versa (i.e., a second request message contains the toggled first value if the external device received a valid response from the IMD to the immediately previously sent first request message containing the second value).

Thus, at least the above mentioned problem may also be solved by a communication system for, in particular wireless, data transfer between an implantable medical device (IMD) and an external device, wherein the IMD is configured to monitor the health status of a patient and/or configured to deliver a therapy signal to the patient, wherein the IMD comprises a processor and a transceiver module configured to bi-directionally exchange messages with the external device (if the IMD is, for example, implanted within the body of the patient), wherein the processor adopts at least a predefined active state and a predefined processing state, wherein processor of the IMD is configured to produce response messages in order to send these response messages from the IMD's transceiver module to the external device, wherein the external device is configured to produce transmit request messages in order to send these messages to the transceiver module of the IMD, wherein each request message comprises a sequence field at a predefined location within the request message which is toggled between at least a first value and a second value associated to the sequence section, wherein a second request message contains the toggled second value if the external device received a valid response from the IMD to the immediately previously sent first request message containing the first value or vice versa (i.e., a second request message contains the toggled first value if the external device received a valid response from the IMD to the immediately previously sent first request message containing the second value).

In one embodiment, the external device is configured to generate and transmit request messages to the transceiver module of the IMD, wherein each request message comprises a sequence field at a predefined location within the request message which is toggled between at least a first value and a second value associated to the sequence section, wherein a second request message contains the toggled second value if the external device received a valid response from the IMD to the immediately previously sent first request message containing the first value or vice versa (i.e., a second request message contains the toggled first value if the external device received a valid response from the IMD to the immediately previously sent first request message containing the second value). In one embodiment the length of the sequence field is 1 bit to 4 bits. If the sequence field is one bit ('sequence bit'), the first value is 1 and the second value 0, for example.

In one embodiment, the request message is a proximity request message, a status request message, a data request message, a monitoring request message, an execution/measurement request message, a program-write message, a program request message, a status request message, an execution request message, or a data request message.

In one embodiment the communication system is configured such that if the IMD receives a request message from the external device containing a value assigned to the sequence field which is equal to the value assigned to the sequence field of the immediately previously received request message, the IMD is configured to send a repeat of its response message, also called a repeat response message, to the external device. Subject to receiving an appropriate message response or response message from the IMD, the external device will assign to the sequence field of the next message a value differing from that of the last sent request message. In cases where the external device does not, however, receive an appropriate response message after a predetermined duration or other met condition, the external device repeats its last sent message and leaves the sequence field within that repeated message unaltered (i.e., the same as it was in the last request command state). The sequence field value of the last request message sent to the IMD from the external device may be stored in memory within the IMD and/or external device as a means for managing whether new commands or retries of unsuccessfully messaging is in effect.

As communication between the IMD and the external device occurs using a channel where the intervening patient anatomy enforces substantial physical separations between in-system send and receive modules, it was recognized that not every request message will reach the IMD and not every response message will reach the external device. It is therefore critical that in any cases where the external device cannot determine whether a sent request message has been processed by the IMD, the system includes a means for the IMD to recognize that the external device is repeating a request message and to ensure that handling of such incoming messaging occurs in a complication-free manner. The sequence field mechanism may be further utilized to access communication data link efficiencies in cases where large memory blocks within the IMD need to be interrogated. Rather than making command requests that include the specific in-IMD memory address targets, commands and system design can be structured in ways that simply call for "interrogation" to proceed. The system (i.e., the IMD and the external device) would be designed such that for a given IMD type key interrogatable information would always reside in prescribed portions of the IMD memory. With this information determined by design, the addressing does not need to be included in the messaging sent between the external device and the IMD. The system would (a priori) know then how much memory needs to be read as part of such sequences and, in turn, issue an "interrogation" style command to the IMD. This such "interrogation" style command would include a sequence field set to a new condition when first sent. If the IMD returns the appropriate first portion of data requested by this process to the external device, the external then changes the sequence field value and can reissue the "interrogation" style command. The recognition of the changed sequence field by the IMD would inform the IMD that the external device had received the first portion of the data requested by the "interrogation" style command and, in turn, respond by sending the 'next' portion of the large block of in-IMD data the external device aims to read. The process would continue until the full block of data was successfully relayed to the external device (retries within such processes being enabled through the sequential transmission of "interrogation" style commands that held the sequence field in a condition matched to the last sent "interrogation style command). As noted above, one or more bits can be used as a sequence field to support this process within the sent request messages. These sequence field states update whenever the external device side infrastructure receives a valid response from the IMD. In cases where all commands and responses pass through the communication channel without corruption, packet loss, or interference, each relayed command from the external device would present values assigned to the sequence field that had flipped and flopped back and forth between the at least two available states. In cases where either the request message was not received by the IMD (and therefore had no capacity to respond) or in cases where the IMD had responded but its response did not reach the external device side infrastructure, the value assigned to the sequence field would hold in a steady condition. Subject to one or more timeout mechanisms (e.g., waiting for a sufficient amount of time to permit the IMD to handle the command and respond), the external device side infrastructure could know that a command had not been received or handled and could resend the unprocessed/unanswered command with the sequence field unchanged. Receiving a command with an unchanged sequence field could tell the IMD that the command was a retry, allowing for the IMD to repeat the command or to just resend the same response. As such, the approach readily facilitates eased handling of large data block segmentation/interrogation needs.

The approach offers a dedicated mechanism within the leadless communication infrastructure to ensure that IMD handling of incoming request messages is always informed regarding the 'newness' vs. 'retry' condition of individual requests—aiding in the avoidance of any potentially problematic conditions that could emerge from restarting command execution/processing. Further, sequence field use/embodiments offer a bandwidth saving transport mechanism for data segmentation (i.e., rather than sending memory or location pointer information from the external device side infrastructure when long writes or reads are needed). The messages themselves can be shorter by simply informing the implant of when it is appropriate to 'hop' to the next segment of data within the IMD. Additionally, the capabilities detailed above are provisioned in a low overhead manner by embedding the functionality in baseline message structures—side-stepping any need for message buffering schemes within the IMD.

The above-mentioned messaging schemes for managing engagements with large blocks of in-IMD memory will certainly involve command and response messages that contain any necessary processor state and sequence fields affiliated with the described communication protocol but they are specifically designed to involve IMD responses that lack the full payload targeted by the command interaction due to interfacing with predefined maximum allowable durations between message transmissions. In such cases, the full target payload is divided across several responses from the IMD that are each sent separately. A field within each of these partial, segmented responses provides a string of bits that, in turn, defines the length (e.g., 1 to 4 bits) of the payload they each carry.

Analogously, at least the above problem is solved by a communication method for data transfer between an implantable medical device (IMD) and an external device. The method has the advantages as were described prior with regard to the system. In particular, the IMD is configured to monitor the health status of a patient and/or configured to deliver a therapy signal to the patient, wherein the IMD comprises a processor and a transceiver module configured to bi-directionally exchange messages with the external device, wherein the processor adopts at least a predefined active state and a predefined processing state, wherein the processor of the IMD produces response messages and sends these response messages from its transceiver module to the external device, wherein each response message comprises a processor state field at a predefined location within the response message wherein
 a predefined first value is assigned to the processor state field as long as the processor is currently in a predefined processing state and
 a predefined second value different from the first value is assigned to the processor state field if the processor is currently not in the processing state.

Accordingly, in one embodiment the external device receiving a response message from the IMD containing the first value assigned to the processor state field waits in sending any new request message (or waits with sending a new request message) to the transceiver module of the IMD until the most recent message contains the second value assigned to the processor state field.

Additionally or alternatively, the external device may produce and send request messages to the transceiver module of the IMD, wherein each request message comprises a sequence field at a predefined location within the request message that is toggled between at least a first value and a second value associated to the sequence field, wherein a second request message contains the toggled second value if the external device received a valid response from the IMD to the immediately previously sent first request message or vice versa.

Thus, at least the above problem may also be solved by a communication method for data transfer between an implantable medical device (IMD) and an external device, wherein the IMD is configured to monitor the health status of a patient and/or configured to deliver a therapy signal to the patient, wherein the IMD comprises a processor and a transceiver module configured to bi-directionally exchange messages with the external device, wherein the processor adopts at least a predefined active state and a predefined processing state, wherein the external device produces request messages in order to send these messages to the transceiver module of the IMD, wherein each request message comprises a sequence field at a predefined location within the request message which is toggled between at least a first value and a second value associated to the sequence field, wherein a second request message contains the toggled second value if the external device received a valid response from the IMD to the immediately previously sent first request message or vice versa.

Alternatively or additionally, the external device produces request messages in order to send these messages to the transceiver module of the IMD, wherein each request message comprises a sequence field at a predefined location within the request message which is toggled between at least a first value and a second value associated to the sequence field, wherein a second request message contains the toggled second value if the external device received a valid response from the IMD to the immediately previously sent first request message or vice versa.

Additionally, in one embodiment, the IMD is configured to send a repeat of its response message to the external device if the IMD receives a request message from the external device containing a value assigned to the sequence field which is equal to the value assigned to the sequence field of the immediately previously received request message.

At least one of the above methods is, for example, realized as a routine or algorithm (to be executed within the external device and/or the IMD, in particular utilizing their respective processors as needed) which is a combination of above and below specified instructions and data definitions that enable the system to perform computational or control operations or which is a syntactic unit that conforms to the rules of a particular programming language and that is composed of declarations and statements or instructions needed for a above and below specified function, task, or problem solution.

Furthermore, a computer program product is disclosed comprising instructions which, when executed by a processor, cause the processor to perform the steps of the above defined method. Accordingly, a computer readable data carrier storing such computer program product is described.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The present invention will now be described in further detail with reference to the accompanying schematic drawing, wherein.

DETAILED DESCRIPTION

Figure 1:
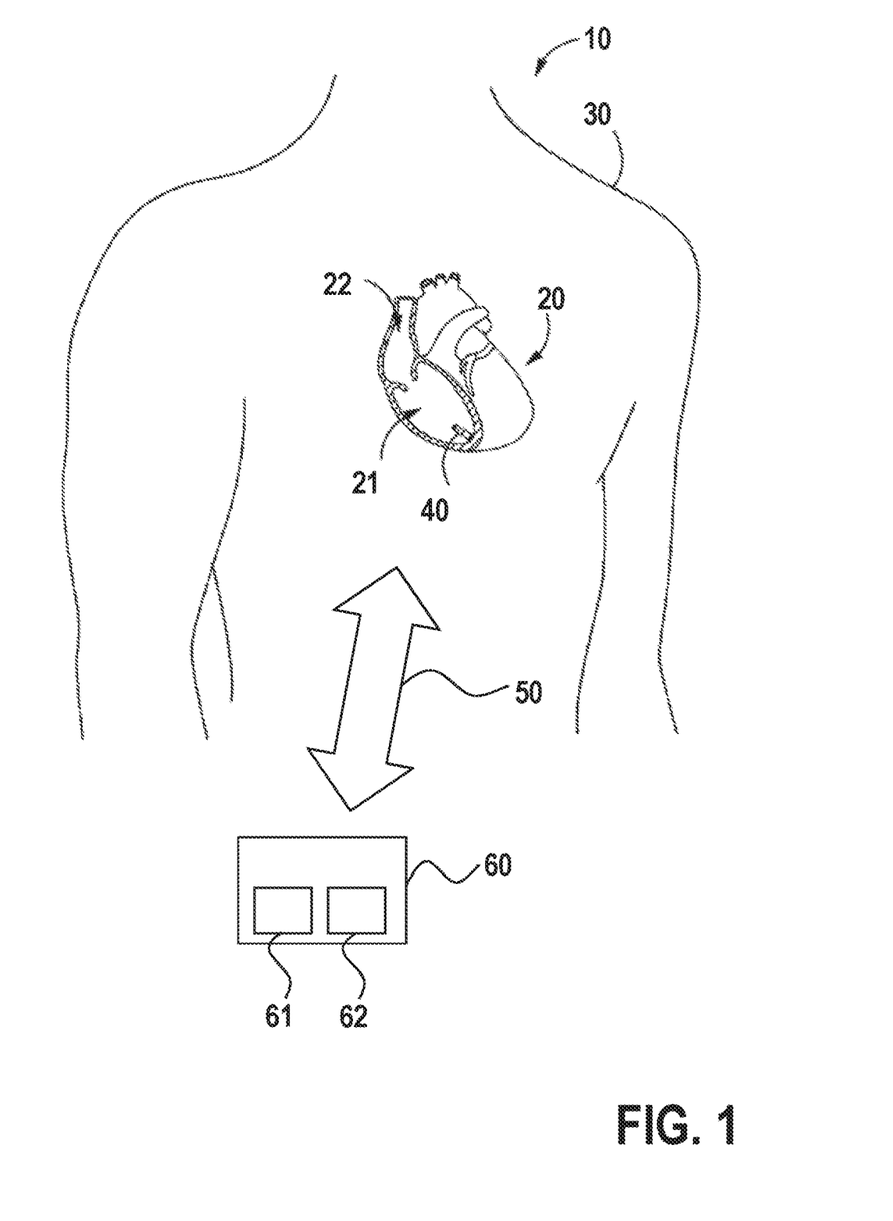
FIG. 1 shows an embodiment of the inventive communication system comprising an implantable leadless pacemaker (ILP) and an external device, wherein the ILP is shown within a cross section of a patient's heart.

FIG. 1 shows an example communication system 10 and a heart 20 (with right ventricle 21 and right atrium 22) of a patient 30. The system 10 comprises a leadless ventricular pacemaker device 40 (hereinafter "ILP 40") as an example for an IMD and an external device 60. ILP 40 may be configured to be implanted within the right ventricle 21 of the heart 20 and to pace this ventricle, sense intrinsic ventricular depolarizations and impedance, and inhibit ventricular pacing in response to detected ventricular depolarization. The ILP 40 may further comprise an accelerometer sensor in order to measure posture of the patient 30 (e.g., by determining acceleration forces due to gravity). A programmer (not shown) may be used to program ILP 40 using the external device 60. The external device 60 is located outside the body is adapted to communicate bi-directionally with the ILP 40.

The ILP 40 may comprise modules such as a processor, a data memory, a signal generator unit for providing treatment signals (e.g., pacing signals), a measurement unit comprising an ECG measuring unit, a DC impedance sensor and the accelerometer sensor, a transceiver for sending and receiving messages to the external device 60, and a power source—each of said modules being electrically connected in some fashion within the IMD. The power source may include a battery, (e.g., a rechargeable or non-rechargeable battery). The data memory module may include any memory type mentioned above. The processor of the ILP 40 may adopt at least the above explained active state and the above explained processing state.

The external device 60 comprises a processor 61 and a transceiver 62 for exchange of messages with the ILP 40 which are electrically connected with each other. Further, the external device 60 may exchange data with other external devices and/or a remote server (not shown). The external device 60 may be the programmer. The bi-directional exchange of messages with the ILP 40 is symbolized by the double-headed arrow 50. The leadless communication of external device 60 with the ILP 40 may be inductive magnetic communication, conducted communication, and/or acoustic communication.

Figure 2:
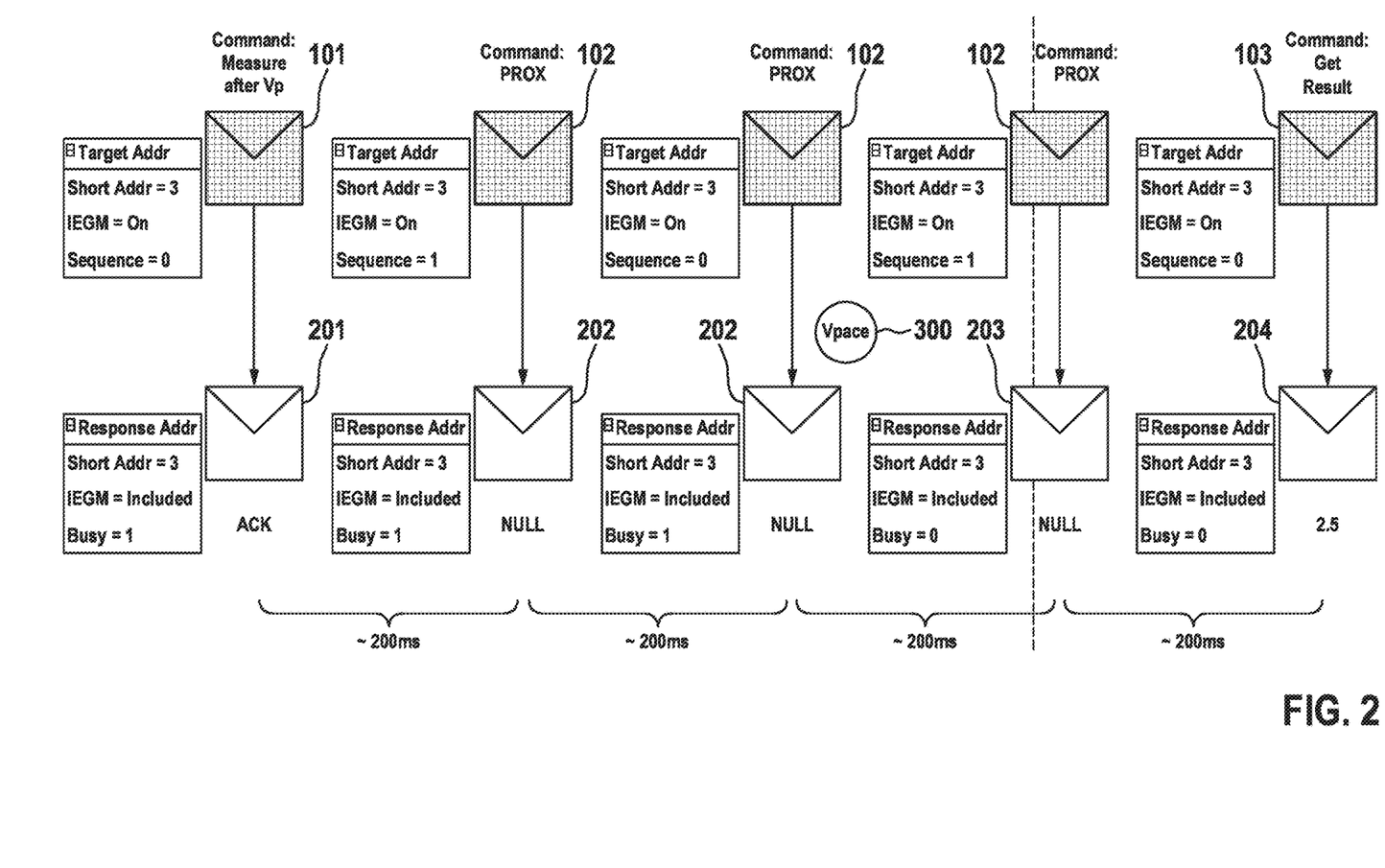
FIG. 2 depicts a flow chart of a first embodiment of an inventive communication method.

In the following, the operation of one embodiment of the communication system and method is explained using FIG. 2. This figure depicts an example sequence of events and interactions, in particular showing a case where the programmer-side infrastructure with the external device 60 requests that the pace amplitude be measured by the ILP 40. The request messages sent by the external device 60 are symbolized by the black envelopes, whereas the white envelopes depict the response messages of the ILP 40. Further, from the respective rectangle on the left side of each envelope, one may derive some key information content or addressing used by the associated message. In particular, the request messages of the external device 60 contain a sequence field ('Sequence' in FIG. 2) as described above with the length of 1 bit. Accordingly, the values 0 and 1 may be associated to the sequence field, which is shown in FIG. 2 as 'Sequence=0' or 'Sequence=1'. Furthermore, the response messages of the ILP may contain the processor state field ('Busy' in FIG. 2) as described above with the length of 1 bit. Accordingly, the values 0 and 1 may be associated to the processor state field, which is shown in FIG. 2 as 'Busy=0' or 'Busy=1'.

In this sequence of events shown in FIG. 2, a Vpace amplitude measurement request message 101 is sent by the external device 60 to the ILP 40 whose processor is in the active state at the beginning. The sequence field within the message starts in an initial stat 'f' '0' ('Sequence=0', though it could have been '1' had it been another point in time). Once the ILP 40 receives the request message for taking the Vpace amplitude measurement, it acknowledges this by sending a response message 201 'ACK' and by also changing the value of the processor state field to '1' ('Busy=1') indicating that the ILP's state is changed to the processing state. The processor awaits the opportunity to collect the measurement and during this time the external device 60 should avoid sending request messages for added support until the IMD completes the requested task. While waiting for the measurement to be conducted and its value to be made available for reporting, the external device side infrastructure sends a series of proximity request messages 102 that only serve to maintain the data link between the ILP 40 and the external device 60 and relay the streaming real-time IEGM to the external device (in the shown example the cadence of the proximity request messages occurs every 200 ms) while waiting for the ILP 40 to complete the requested measurement. Throughout this process the external device monitors the value of the processor state field in the ILP's response messages 202, 203 being so called Null responses (also often referred to as Acknowledge responses). Once the Vpace event occurs (see reference number 300 in FIG. 2), the ILP 40 conducts the measurement of Vpace. The response message 203 of the ILP 40 is then sent with the changed processor state field (changed from '1' to '0') to make the external device 60 known that the ILP 40 returned to the active state and can now be commanded to report the available measurement value. The external device 60 then sends a message 103 requesting the results of the measurement and after receipt of the request message 103 the ILP 40 immediately sends a response message 204 reporting (in this particular example) an amplitude of 2.5 V. In this response message 204 the processor state field is associated with the value '0' because the processor of ILP 40 finishes this request right after the receipt by sending the measured value with response message 204.

An alternative embodiment could have had the IMD simply report back the amplitude of 2.5 V, which is done in following cycle 204 instead of sending the Null response 203. This approach would return the amplitude to the external device without having the IMD first report on its availability and without having any reliance upon external device to issue another data collection command. In such a response the 'busy' bit would be set to '0' in the same way that it is handled in response 203.

Regarding the sequence field, one can derive from FIG. 2 that with each request message 101, 102, 103 the sequence field is toggled, namely from the initial value '0' in the first request message 101 to the second value '1' in the second request message 102 to the first value '0' in the third request message 102 to the second value '1' in the fourth request message 102 and finally to the first value '0' in the last request message 103 because the external device 60 did receive an appropriate response from the ILP 40 with regard to the previous request message as part of each involved data messaging cycle. In case one of the request messages 101, 102, 103 would not have reached the ILP 40, there would be no response from the ILP 40 and the value of the sequence field would not be changed. (Note: The sequence field would also not have changed on any cycle where a response from the IMD had not successfully reached the external device 60). Accordingly, after sending the respective request message by the external device 60 the ILP would derive from this request message that the value of the sequence field is the same as in the previous request message. Because the processor of the ILP 40 would then conclude that one interim request message was not properly received or processed (i.e., one response was missed by the external device) ILP 40 would 1.) rerun the routine that had been requested by the recognized command and respond, or, likely more optimally, 2.) simply re-send the response to the external device 60.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A communication system for a wireless message transfer between an implantable medical device (IMD) and an external device, wherein the IMD is configured to monitor a health status of a patient and/or configured to deliver a therapy signal to the patient, wherein the IMD comprises a processor and a transceiver module configured to bi-directionally exchange messages with the external device via a single threaded command architecture, wherein the processor is configured to switch between a predefined active state and a predefined processing state, wherein the external device is configured to produce and send request messages to a transceiver module of the IMD, wherein each request message comprises a sequence field at a predefined location within the request message which is toggled between at least a first value and a second value associated to the sequence field, wherein the request messages comprise a first request message and a second request message, wherein when the external device receives a valid response from the IMD to an immediately previously sent first request message, the second request message contains the second value, and wherein when the external device does not receive a valid response from the IMD to an immediately previously sent first request message, the second request message contains the first value.

2. The communication system of claim 1, wherein the length of the sequence field is 1 bit to 4 bits.

3. The communication system of claim 1, wherein at least one request message is a proximity request message, a status request message, a data request message, a monitoring request message, an execution/measurement request message, a program-write message, a program request message, or an execution request message.

4. The communication system of claim 1 which is configured such that when the IMD receives a request message from the external device containing a value assigned to the sequence field which is equal to a value assigned to a sequence field of an immediately previously received request message, the IMD is configured to send a repeat response message to the external device.

5. The communication system of claim 1, wherein a break the single-threaded architecture is prevented by the steps of:
wherein when the external device receives a valid response from the IMD to an immediately previously sent first request message, the second request message contains the toggled second value, and wherein when the external device does not receive a valid response from the IMD to an immediately previously sent first request message, the second request message contains the first value.

6. A communication method for data transfer between an implantable medical device (IMD) and an external device, wherein the IMD is configured to monitor a health status of a patient and/or configured to deliver a therapy signal to the patient, wherein the IMD comprises a processor and a transceiver module configured to bi-directionally exchange messages with the external device via a single threaded command architecture, the method comprising: switching the processor between a predefined active state and a predefined processing state; producing request messages by the external device and sending the request messages to the transceiver module of the IMD, wherein each request message comprises a sequence field at a predefined location within the request message which is toggled between at least a first value and a second value associated to the sequence field, wherein the request messages comprise a first request message and a second request message; causing the second request message to contains the second value when the external device receives a valid response from the IMD to an immediately previously sent first request message; and causing the second request message to contain the first value when the external device not receive a valid response from the IMD to an immediately previously sent first request message.

7. The communication method of claim 6, wherein a break the single-threaded architecture is prevented by the steps of:
causing the second request message to contain the second value when the external device receives a valid response from the IMD to an immediately previously sent first request message; and causing the second request message to contain the first value when the external device not receive a valid response from the IMD to an immediately previously sent first request message.

8. A communication method for data transfer between an implantable medical device (IMD) and an external device, wherein the IMD is configured to monitor the health status of a patient and/or configured to deliver a therapy signal to the patient, wherein the IMD comprises a processor and a transceiver module configured to bi-directionally exchange messages with the external device, wherein the processor adopts at least a predefined active state and a predefined processing state, wherein the processor of the IMD produces response messages and sends these response messages from the transceiver module to the external device, wherein each response message comprises a processor state field at a predefined location within the response message wherein:

a predefined first value is assigned to the processor state field as long as the processor is currently in a predefined processing state, and a predefined second value different from the first value is assigned to the processor state field if the processor is currently not in the processing state;

wherein, if the IMD receives a request message from the external device containing a value assigned to the sequence field which is equal to the value assigned to the sequence field of the immediately previously received request message, the IMD sends a repeat message to the external device.

* * * * *